United States Patent [19]

Bernardi et al.

[11] Patent Number: 4,632,990

[45] Date of Patent: Dec. 30, 1986

[54] ERGOLINE CARBOXAMIDES

[75] Inventors: Luigi Bernardi, Milan; Enzo Brambilla, Mariano Comense; Laura Chiodini, Busto Arsizio; Enrico di Salle; Daniela Ruggieri, both of Milan; Osvaldo Sapini, Gallarate; Aldemio Temperilli, Milan, all of Italy

[73] Assignee: Farmitalia Carlo Erba S.p.A., Milan, Italy

[21] Appl. No.: 484,477

[22] Filed: Apr. 13, 1983

[30] Foreign Application Priority Data

Apr. 13, 1982 [GB] United Kingdom ............... 8210697

[51] Int. Cl.$^4$ ............... A61K 31/48; B07D 457/06; C07D 239/42
[52] U.S. Cl. .................. 544/329; 544/310; 544/317; 544/318; 544/319; 546/67; 546/69
[58] Field of Search ............. 544/318, 319, 329, 328; 546/69; 514/288, 256

[56] References Cited

U.S. PATENT DOCUMENTS

| | | | |
|---|---|---|---|
| 3,218,324 | 11/1965 | Hofmann et al. | 546/69 |
| 3,238,211 | 3/1966 | Camerino et al. | 546/69 |
| 3,583,992 | 6/1971 | Hofmann et al. | 424/261 |
| 3,904,633 | 9/1975 | Karacsony et al. | 424/261 |
| 3,966,941 | 6/1976 | Semonsky et al. | 424/261 |
| 4,035,501 | 7/1977 | Hauth | 546/69 |
| 4,054,660 | 10/1977 | Clemens et al. | 424/261 |
| 4,101,552 | 7/1978 | Karacsony et al. | 546/69 |
| 4,147,789 | 4/1979 | Stutz et al. | 544/319 |
| 4,291,031 | 9/1981 | Takaya et al. | 544/21 |

FOREIGN PATENT DOCUMENTS

| | | | |
|---|---|---|---|
| 70562 | 1/1963 | European Pat. Off. | 546/67 |
| 1339406 | 3/1964 | France | 424/261 |
| 459243 | 9/1968 | Switzerland | 546/69 |
| 578565 | 8/1976 | Switzerland | 546/69 |
| 2058746 | 4/1981 | United Kingdom | 424/261 |
| 2074566 | 11/1981 | United Kingdom | 546/69 |

OTHER PUBLICATIONS

Guyton, Arthur C., *Medical Physiology*, 6th, W. B. Saunders, Philadelphia, 1981.

*Primary Examiner*—Glenna M. Hendricks
*Attorney, Agent, or Firm*—Oblon, Fisher, Spivak, McClelland & Maier

[57] ABSTRACT

There are provided ergoline derivatives of the formula:

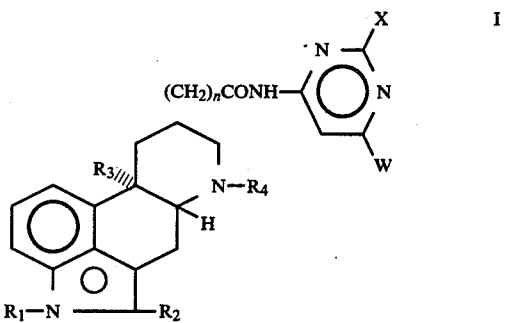

wherein $R_1$ represents a hydrogen atom or a methyl group, $R_2$ represents a hydrogen or halogen atom or a methyl group, $R_3$ represents a hydrogen atom or a methoxy group, $R_4$ represents a hydrocarbon group having from 1 to 4 carbon atoms; each of X and W independently represents a hydrogen atom, a methyl group, a chlorine atom or a methoxy group, and n is 0, 1 or 2. A method for their preparation is also provided. The compounds have strong antiprolactin activity.

11 Claims, No Drawings

ERGOLINE CARBOXAMIDES

DESCRIPTION

The invention relates to ergoline derivatives, to processes for their preparation, and to pharmaceutical compositions containing them.

The invention provides ergoline derivatives having the general formula I

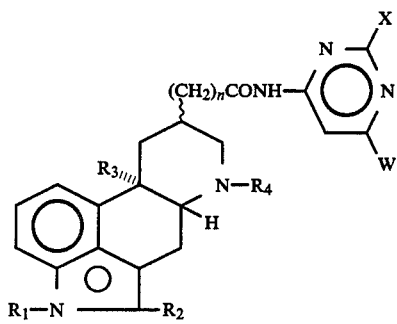

I wherein $R_1$ represents a hydrogen atom or a methyl group, $R_2$ represents a hydrogen or halogen atom or a methyl group, $R_3$ represents a hydrogen atom or a methoxy group, $R_4$ represents a hydrocarbon group having from 1 to 4 carbon atoms; each of X and W independently represents a hydrogen atom, a methyl group, a chlorine atom or a methoxy group, and n is 0, 1 or 2 and further provides pharmaceutically acceptable salt of such ergoline derivatives.

The invention also provides a process for the preparation of the ergoline derivatives of the general formula I as above defined, which process comprises reacting an activated ester of an ergoline carboxylic acid of the general formula II, wherein $R_1$, $R_2$, $R_3$, $R_4$ and n are as above defined, with 4-amino-pyrimidine of the general formula III, wherein X and W are as above defined,

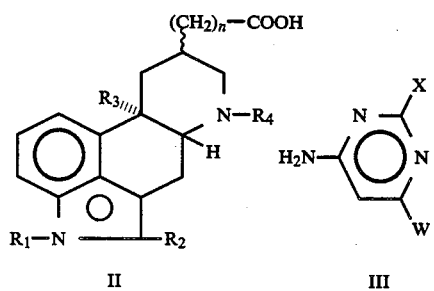

II    III in a solvent such as tetrahydrofuran, dimethyl-formamide or dioxan at a temperature of from 50° to 100° C. for a period of 24 to 48 hours. A suitable activated ester is that prepared by reacting an ergoline acid of formula II with 1-hydroxybenzotriazole in the presence of N,N'-dicyclohexylcarbodiimide in tetrahydrofuran at reflux for a period of from 2 to 5 hours.

The ergoline amides according to the invention are generally isolated by techniques commonly used in chemistry and further purified by crystallization, chromatography or salt formation.

The ergoline amides according to the invention and their pharmaceutically acceptable salts have been shown to possess a strong anti prolactin activity in rats. The prolactin secretion inhibitory action of the compounds has been indirectly evaluated by determining the egg-nidation inhibitory action in rats. For the ergoline derivatives this activity is considered to be correlated with the anti-prolactin activity (E. Fluckiger and E. Del Pozo, Handb. Exp. Pharmac. 49, 615, 1978), prolactin being the only hypophysial hormone involved in the maintenance of the first part of pregnancy in rats (W. K. Morischige and I. Rothchild, Endocrinology 95, 260, 1974).

Pregnant Sprague Dowley rats weighing 200–250 g were used. The compounds to be tested, dissolved in diluted mineral acids, were administered orally to groups from six to eight rats on day 5 of pregnancy. The animals were sacrificed on day 14 and the uteri were examined. The absence of implantation sites was taken as the criterion of anti-prolactin activity. Several doses were tested for the $ED_{50}$ evaluation. As reference standard Bromocryptine was used. The results are reported in the Table below.

TABLE

| Compounds | Nidation inhibition in rats, $ED_{50}$ mg/kg p.o. |
| --- | --- |
| N—(2',6'-dimethyl-4'-pyrimidyl)-6-methylergoline-8β-carboxamide | 1.8 |
| N—(2',6'-dimethyl-4'-pyrimidyl)-2,6-dimethylergoline-8β-carboxamide | 0.5–1 |
| N—(2',6'-dimethyl-4'-pyrimidyl)-6-propylergoline-8β-carboxamide | 0.3 |
| N—(2',6'-dimethyl-4'-pyrimidyl)-6-allylergoline-8β-carboxamide | 1–0.5 |
| 2-bromo-α-ergocryptine (as reference compound) (Bromocryptine) | 5.7 |

From the Table it appears that the new ergoline derivatives are from 3 to 19 times more active than Bromocryptine as nidation inhibitors. From the above results it is logical to predict that the new ergoline derivatives may find an advantageous clinical exploitation in all the situations in which it is desirable to reduce prolactin levels such as inhibition of puerperal lactation, inhibition of galactorrhoea and treatment of infertility due to hyperprolactinaemia. The compounds, for their probable dopamine agonist activity, may also find utility, like Bromocryptine for the treatment of Parkinson's disease and acromegaly. Accordingly, the invention further provides a pharmaceutical compostion comprising an ergoline derivative having the general formula I as above defined or a pharmaceutically acceptable salt thereof in admixture with a pharmaceutically acceptable diluent or carrier.

The following Examples illustrate the invention.

EXAMPLE 1

N-(2',6'-dimethyl-4'-pyrimidyl)-6-methylergoline-8β-carboxamide

A mixture of 16.2 g of 6-methylergoline-8β-carboxylic acid, 16.2 g of 1-hydroxybenzotriazole and 74.16 g of N,N'-dicyclohexylcarbodiimide in 1800 ml of tetrahydrofuran was refluxed for 4 hours. Then 7.39 g of 4-amino-2,6-dimethylpyrimidine were added and refluxing was continued for 18 hours. The precipitated dicyclohexyurea was removed by filtration, the filtrate was evaporated to dryness in vacuo and the solid residue was dissolved in chloroform and then extracted with water containing 5 ml of hydrochloric acid. The acid extracts were neutralized with an excess of sodium bicarbonate and then extracted with chloroform. The residue of the organic layer was crystallized from methanol to give 16 g of the title compound, m.p. 258°–260° C.

EXAMPLE 2

N-(2',6'-dimethyl-4'-pyrimidyl)-1,6-dimethylergoline-8β-carboxamide

Operating as in Example 1, but employing 1,6-dimethyl-ergoline-8β-carboxylic acid in place of 6-methylergoline-8β-carboxylic acid, the title compound m.p. 201°–203° C., was obtained in 68% yield.

EXAMPLE 3

N-(4'-pyrimidyl)-6-methylergoline-8β-carboxamide

Operating as in Example 1, but employing 4-aminopyrimidine in place of 4-amino-2,6-dimethylpyrimidine, the title compound, m.p. 227°–229° C., was obtained in 75% yield.

EXAMPLE 4

N-(2',6'-dimethyl-4'-pyrimidyl)-2,6-dimethylergoline-8β-carboxamide

Operating as in Example 1, but employing 2,6-dimethymergoline-8β-carboxylic acid in place of 6-methylergoline-8β-carboxylic acid, the title compound, m.p. 152°–154° C., was obtained in 72% yield.

EXAMPLE 5

N-(2',6'-dimethyl-4'-pyrimidyl)-6-propylergoline-8β-carboxamide

Operating as in Example 1, but employing 6-propylergoline-8β-carboxylic acid in place of 6-methylergoline-8β-carboxylic acid, the title compound, m.p. 120°–122° C., was obtained in 65% yield.

EXAMPLE 6

N-(2',6'-dimethyl-4-pyrimidyl)-6-allylergoline-8β-carboxamide

Operating as in Example 1, but employing 6-allylergoline-8β-carboxylic acid in place of 6-methylergoline-8β-carboxylic acid, the title compound, m.p. 182°–186° C., was obtained in 70% yield.

EXAMPLE 7

N-(2',6'-dimethyl-4'-pyrimidyl)-6-isopropylergoline-8β-carboxamide

Operating as in Example 1, but employing 6-isopropylergoline-8β-carboxylic acid in place of 6-methylergoline-8β-carboxylic acid, the title compound, m.p. 116°–118° C., was obtained in 69% yield.

EXAMPLE 8

N-(2',6'-dimethyl-4'-pyrimidyl)-1-methyl-6-allylergoline-8β-carboxamide

Operating as in Example 1, but employing 1-methyl-6-allylergoline-8β-carboxylic acid in place of 6-methylergoline-8β-carboxylic acid, the title compound, m.p. 168°–170° C., was obtained in 73% yield.

EXAMPLE 9

N-(4'-pyrimidyl)-10-methoxy-6-methylergoline-8β-carboxamide

Operating as in Example 1, but employing 10-methoxy-6-methylergoline-8β-carboxylic acid, the title compound, m.p. 246°–247° C., was obtained in 70% yield.

EXAMPLE 10

N-(2',6'-dimethyl-4'-pyrimidyl)-6-methylergoline-8α-carboxamide

Operating as in Example 1, but employing 6-methylergoline-8α-carboxylic acid, the title compound, m.p. 258°–260° C., was obtained in 71% yield.

EXAMPLE 11

N-(2',6'-dimethyl-4'-pyrimidyl)-6-propylergoline-8α-carboxamide

Operating as in Example 1, but employing 6-propylergoline-8α-carboxylic acid, the title compound, m.p. 204°–205° C., was obtained in 60% yield.

EXAMPLE 12

2-(6-methylergolinyl-8β)-N-2',6'-dimethyl-4'-pyrimidinyl-acetamide

Operating as in Example 1, but employing 6-methylergolinyl-8β-acetic acid, the title compound, m.p. 245°–247° C., was obtained in 68% yield.

EXAMPLE 13

3-(6-methylergolinyl-8β)-N-2',6'-dimethyl-4'-pyrimidinyl-propionamide

Operating as in Example 1, but employing 3-(6-methylergolinyl-8β)-propionic acid, the title compound, m.p. 195°–196° C., was obtained in 70% yield.

We claim:

1. An ergoline selected from the group consisting of N-(2',6'dimethyl-4'-pyrimidyl)-6-methylergoline-8β-carboxamide, N-(2',6'-dimethyl-4'-pyrimidyl)-1,6-dimethylergoline-8β-carboxamide, N-(4'-pyrimidyl)-6-methylergoline-8β-carboxamide, N-(2',6'-dimethyl-4'-pyrimidyl)-2,6-dimethylergoline-8β-carboxamide, N-(2',6'-dimethyl-4'-pyrimidyl)-6-propylergoline-8β-carboxamide, N-(2',6'-dimethyl-4'-pyrimidyl)-6-allylergoline-8β-carboxamide, N-(2',6'-dimethyl-4'-pyrimidyl)-6-isopropylergoline-8β-carboxamide, N-(2',6'-dimethyl-4'-pyrimidyl)-1-methyl-6-allylergoline-8β-carboxamide, N-(2',6'-dimethyl-4'-pyrimidyl)-6-methylergoline-8α -carboxamide, and N-(2',6'-dimethyl-4'-pyrimidyl)-6-propylergoline-8α-carboxamide.

2. An ergoline according to claim 1, which is N-(2',6'-dimethyl-4'-pyrimidyl)-6-methylergoline-8β-carboxamide.

3. An ergoline according to claim 1, which is N-(2'-6'-dimethyl-4'-pyrimidyl)-1,6-dimethylergoline-8β-carboxamide.

4. An ergoline according to claim 1, which is N-(4'-pyrimidyl)-6-methylergoline-8β-carboxamide.

5. An ergoline according to claim 1, which is N-(2',6'-dimethyl-4'-pyrimidyl)-2,6-dimethylergoline-8β-carboxamide.

6. An ergoline according to claim 1, which is N-(2',6'-dimethyl-4'-pyrimidyl)-6-propylergoline-8β-carboxamide.

7. An ergoline according to claim 1, which is N-(2',6'-dimethyl-4'-pyrimidyl)-6-allylergoline-8β-carboxamide.

8. An ergoline according to claim 1, which is N-(2',6'-dimethyl-4'-pyrimidyl)-6-isopropylergoline-8β-carboxamide.

9. An ergoline according to claim 1, which is N-(2',6'-dimethyl-4'-pyrimidyl)-1-methyl-6-allylergoline-8β-carboxamide.

10. An ergoline according to claim 1, which is N-(2',6'-dimethyl-4'-pyrimidyl)-6-methylergoline-8α-carboxamide.

11. An ergoline according to claim 1, which is N-(2',6'-dimethyl-4'-pyrimidyl)-6-propylergoline-8α-carboxamide.

* * * * *